(12) United States Patent
Kondo et al.

(10) Patent No.: US 10,408,751 B2
(45) Date of Patent: Sep. 10, 2019

(54) MEASUREMENT METHOD AND MEASUREMENT SYSTEM

(71) Applicant: Murata Manufacturing Co., Ltd., Nagaokakyo-shi, Kyoto-fu (JP)

(72) Inventors: Takashi Kondo, Nagaokakyo (JP); Seiji Kamba, Nagaokakyo (JP); Naoki Kawara, Nagaokakyo (JP); Takashi Shimizu, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 325 days.

(21) Appl. No.: 15/341,438

(22) Filed: Nov. 2, 2016

(65) Prior Publication Data

US 2017/0074790 A1 Mar. 16, 2017

Related U.S. Application Data (63) Continuation of application No. PCT/JP2015/058664, filed on Mar. 23, 2015.

(30) Foreign Application Priority Data

Jun. 3, 2014 (JP) ................................ 2014-114809

(51) Int. Cl.
*G01N 21/3586* (2014.01)
*G01N 21/01* (2006.01)
(Continued)

(52) U.S. Cl.
CPC ......... *G01N 21/3586* (2013.01); *G01N 21/01* (2013.01); *G01N 21/3581* (2013.01); *G01N 33/0009* (2013.01); *G01N 2021/3595* (2013.01)

(58) Field of Classification Search
CPC .................................................. G01N 21/3586
(Continued)

(56) References Cited

U.S. PATENT DOCUMENTS

| 4,583,396 A | 4/1986 | Defence |
| 7,648,550 B2 | 1/2010 | Beall et al. |

(Continued)

FOREIGN PATENT DOCUMENTS

| JP | S5940142 A | 3/1984 |
| JP | H0336175 B2 | 5/1991 |

(Continued)

OTHER PUBLICATIONS

International Search Report issued for PCT/JP2015/058664, dated Jun. 9, 2015.

(Continued)

*Primary Examiner* — John Fitzgerald
*Assistant Examiner* — Rodney T Frank
(74) *Attorney, Agent, or Firm* — Arent Fox LLP (57) ABSTRACT

A measurement method measures an amount of substance of an analyte in a sample fluid passing through a perforated structure having a pair of principal surfaces opposed to each other and having a plurality of cavity portions extending through both of the principal surfaces. An elapsed time from a time when the sample fluid begins passing through the perforated structure or a predetermined time thereafter to a time when a characteristic value of the perforated structure reaches a predetermined threshold. The elapsed time is used to determine the amount (the concentration) of substance of the analyte.

16 Claims, 9 Drawing Sheets

(51) Int. Cl.
  *G01N 21/3581*   (2014.01)
  *G01N 33/00*   (2006.01)
  *G01N 21/35*   (2014.01)

(58) Field of Classification Search
  USPC ..................................................... 73/28.04
  See application file for complete search history.

(56) References Cited

U.S. PATENT DOCUMENTS

| | | |
|---|---|---|
| 7,826,042 B2 | 11/2010 | Yamamichi et al. |
| 8,023,109 B2 | 9/2011 | Yamamichi et al. |
| 2008/0047243 A1 | 2/2008 | Beall et al. |
| 2009/0009756 A1 | 1/2009 | Yamamichi et al. |
| 2011/0019195 A1 | 1/2011 | Yamamichi et al. |
| 2015/0129769 A1 | 5/2015 | Kamba et al. |

FOREIGN PATENT DOCUMENTS

| | | |
|---|---|---|
| JP | H10-267843 A | 10/1998 |
| JP | 2005-133580 A | 5/2005 |
| JP | 2005-283556 A | 10/2005 |
| JP | 2009-294060 A | 12/2009 |
| JP | 2010-501468 A | 1/2010 |
| JP | 2014-055781 A | 3/2014 |
| WO | WO 2012/132128 A1 | 10/2012 |
| WO | WO 2014/017430 A1 | 7/2016 |

OTHER PUBLICATIONS

Written Opinion of the International Searching Authority issued for PCT/JP2015/058664, dated Jun. 9, 2015.

MEASUREMENT METHOD AND MEASUREMENT SYSTEM

CROSS REFERENCE TO RELATED APPLICATIONS

The present application is a continuation of International application No. PCT/JP2015/058664, filed Mar. 23, 2015, which claims priority to Japanese Patent Application No. 2014-114809, filed Jun. 3, 2014, the entire contents of each of which are incorporated herein by reference.

TECHNICAL FIELD

The present invention relates to a measurement method and measurement system for measuring characteristics of an analyte.

BACKGROUND ART

There are known methods for measuring characteristics of an analyte (e.g., the amount of the analyte) by accumulating the analyte on a perforated structure (e.g., metal mesh) and analyzing various changes in characteristics of the perforated structure resulting from the presence of the analyte.

One exemplary method is disclosed in Patent Document (International Publication No. 2014-017430). In that method, electromagnetic waves are emitted to a perforated structure having cavity portions in a state where an analyte is held in the perforated structure, electromagnetic waves that have passed through the perforated structure are detected, and the characteristics of the analyte are measured based on changes in frequency characteristics of transmittance caused by the presence of the analyte.

SUMMARY OF INVENTION

Technical Problem

In the measurement method disclosed, for example, in Patent Document 1, there are problems when there are large changes in concentration of an analyte among samples (sample fluids). If all the samples are filtered in the same way through the perforated structure for a certain length of time and the characteristics of the perforated structure holding the analytes are measured after the filtration, it is not possible to obtain accurate measured values when the concentration of the analyte is either less than a lower limit of quantification or more than an upper limit of quantification. Thus, the known measurement method suffers the problem that, in the case where changes in characteristics of an analyte, such as changes in concentration of an analyte, are large among samples, not all of the samples are measured with high sensitivity.

One approach to addressing the situation where the concentration of the analyte is less than the lower limit of quantification is to extend the period of time for which a sample is filtered, increase the amount of the analyte accumulated in the perforated structure, and perform measurement again. One approach to addressing the situation where the concentration of the analyte exceeds the upper limit of quantification is to filter the sample again with a shortened period of time, reduce the amount of the analyte accumulated in the perforated structure, and then perform measurement again. However, in both cases, many additional steps and significant time are required for the entire measurement, and there is a problem in that measurement of characteristics of an analyte is not efficient.

In view of the foregoing, it is an object of the present invention to provide a measurement method and measurement system capable of performing measurement with high sensitivity and high efficiency even when changes in characteristics of an analyte, such as changes in concentration of an analyte, are large among samples.

Solution to Problem

The present invention provides a measurement method for measuring an amount of substance of an analyte. The measurement method includes accumulating the analyte by causing a sample fluid containing the analyte to pass through a perforated structure having a pair of principal surfaces opposed to each other and having a plurality of cavity portions extending through both of the principal surfaces, measuring an elapsed time beginning when the accumulating step begins or after a predetermined time period has elapsed after the beginning of the accumulating step to a time when a characteristic value of the perforated structure reaches a predetermined threshold, and converting the elapsed time into the amount of substance of the analyte (i.e., determining the quantity of the substance of the analyte as a function of the elapsed time).

During the accumulating step, a flow velocity of the sample fluid may preferably be optimized based on the characteristic value of the perforated structure.

The characteristic value may preferably be a parameter relating to frequency characteristics of the perforated structure when electromagnetic waves are emitted thereto.

The characteristic value may preferably include one or more of a velocity of the sample fluid passing through the perforated structure, a quantity of flow through the perforated structure, and a pressure loss occurring when the sample fluid passes through the perforated structure.

The present invention also provides a measurement system for measuring characteristics of an analyte. The measurement system includes a perforated structure having a pair of principal surfaces opposed to each other and having a plurality of cavity portions extending through both of the principal surfaces, an intake and exhaust mechanism for causing a sample fluid containing the analyte to pass through the perforated structure, a detection mechanism for detecting a characteristic value of the perforated structure holding the analyte while the sample fluid passes therethrough, a time measuring mechanism for measuring an elapsed time from a point in time after the sample fluid starts passing through the perforated structure, and a quantification mechanism for converting the elapsed time at a time when the characteristic value reaches a predetermined threshold into an amount of substance of the analyte.

Advantageous Effects of Invention

According to the present invention, a measurement method and measurement system capable of performing measurement with high sensitivity and high efficiency even when changes in characteristics of an analyte, such as changes in concentration of an analyte, are large among samples can be provided.

DESCRIPTION OF THE PREFERRED EMBODIMENTS

Preferred embodiments of the present invention are described with reference to the drawings. The same reference numerals are used in the same or corresponding portions in the drawings, and the description thereof is not repeated.

Figure 1:
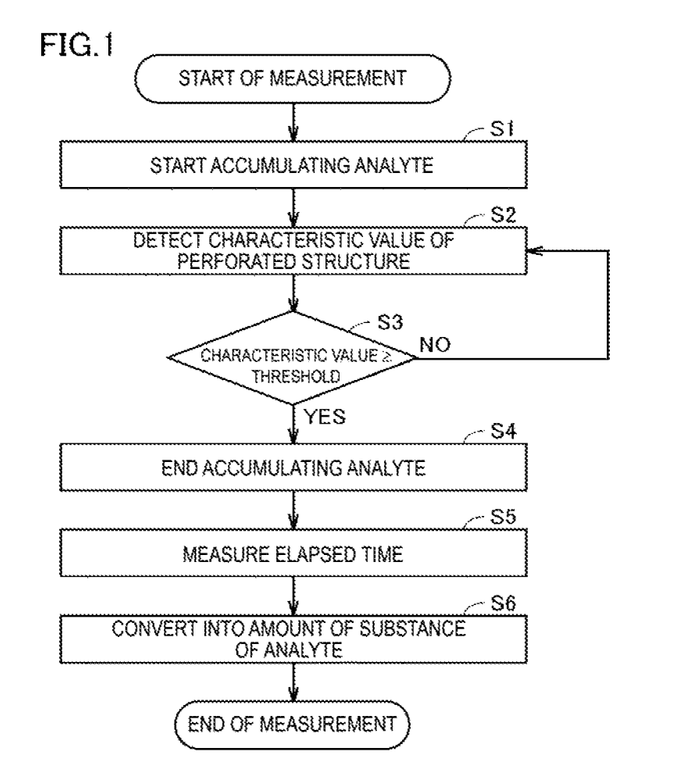
FIG. 1 is a flow chart that illustrates a procedure in a measurement method according to the present invention.

A measurement method in accordance with one embodiment of the present invention is described with reference to the flow chart illustrated in FIG. 1. First, a characteristic value of a perforated structure is continuously detected (S2) for at least a time period preferably beginning when the analyte begins accumulating on the perforated structure (e.g., when a suction pump is actuated) or an elapsed time after the analyte begins accumulating on the perforated structure and continuing until the measured characteristic value of the perforated structure exceeds a threshold value (S3) at which time the further accumulation of the analyte stops (e.g., by turning off the suction pump) (S4). The detection of the characteristic and its comparison to the threshold value preferably is continuous. However, as used herein, continuous includes intermittent detection and comparison over a continuous time period. As shown in FIG. 1, at each detection instant (S2) the measured characteristic value is compared with the predetermined threshold. If the characteristic value is less than the threshold (S3), the process loops back to step S2 and the detection of the characteristic value is repeated. When the characteristic value becomes equal to or larger than the threshold (reaches the threshold), the accumulation of the analyte ends (S4) (e.g., by turning off the suction pump or otherwise stopping flow of the fluid containing the analyte through the perforated structure). The elapsed time from the start of accumulating the analyte (S1) until the accumulation of the analyte stops (S4) is measured (S5). Finally, the elapsed time is used to determine the amount of substance of the analyte (S6) and the measurement process ends.

One example of the elapsed time after the analyte begins accumulating on the perforated structure may be the time when a change in the characteristic value of the perforated structure starts to occur in comparison with that at the time when the accumulation of the sample fluid starts.

Examples of the "amount of substance of an analyte" measured in the present invention includes, but is not limited to, the concentration and content of the analyte in a fluid (e.g., gas or liquid) sample.

The "characteristic value" of the perforated structure detected in the present invention is not particularly limited. One example thereof may be a parameter relating to frequency characteristics of the perforated structure when electromagnetic waves are emitted thereto. Non-limiting examples of the parameter may include a frequency at a minimum value of a dip waveform occurring in frequency characteristics of electromagnetic waves that have been forward scattered in (passed through) the perforated structure, a frequency at a maximum value of a peak waveform occurring in frequency characteristics of electromagnetic waves that have been backward scattered (reflected), transmittance and reflectance of electromagnetic waves at a specific frequency, and the amount of change (rate of change) of each of them.

A dip waveform is a waveform in a portion having a valley (convex downward) shape that is partially seen in frequency characteristics (e.g., transmittance spectral) of a perforated structure in a frequency range where the ratio of detected electromagnetic waves to emitted electromagnetic waves (e.g., transmittance of electromagnetic waves) is relatively large. A peak waveform is a waveform having a peak (convex upward) shape that is partially seen in frequency characteristics (e.g., reflectance spectral) of a perforated structure in a frequency range where the ratio of detected electromagnetic waves to emitted electromagnetic waves (e.g., reflectance of electromagnetic waves) is relatively small.

The electromagnetic waves used in detection of frequency characteristics may be, for example, electromagnetic waves that can generate scattering in accordance with the configuration of the perforated structure. Specific examples thereof may include radio waves, infrared rays, visible rays, ultraviolet rays, X rays, and gamma rays. From the viewpoint of miniaturization or the like of a device used in a measurement system, visible rays or infrared rays may preferably be used. To measure a minute quantity of an analyte with high sensitivity, electromagnetic waves that are preferably in a frequency band from 1 GHz to 1 PHz may be used, and more preferably, terahertz waves in a frequency band from 20 GHz to 200 THz may be used. The frequency characteristics of the perforated structure can be detected, for example, by terahertz time-domain spectroscopy (THz-TDS), Fourier transform infrared spectroscopy (FT-IR), or the like using the above-described electromagnetic waves.

Other non-limiting examples of the measured characteristic value of the perforated structure may include the velocity of a sample fluid passing through the perforated structure, the quantity of flow of the sample fluid, and the pressure loss occurring when the sample fluid passes through the perforated structure. In the case where the fluid has a known cross-sectional area in a direction perpendicular to the direction in which the fluid moves at a location where the characteristic value is measured, because the velocity and quantity of flow of the fluid are proportional to each other, when either one of the velocity and quantity of flow of the sample fluid is detected, the other can be determined by calculation.

Where the characteristic value is the velocity of the sample fluid passing through the perforated structure, the quantity of flow of the sample fluid, or the pressure loss occurring when the sample fluid passes through the perforated structure, the characteristic value and time may be correlated with each other (at least during a time period $T_A$ during which the characteristic value varies at a constant rate). This correlation may be expressed as, for example, an m-th-order function, a linear function or a zero-order function (i.e., the characteristic value does not change over time).

The measurement time period during which the characteristic values are measured/detected is preferably less than the time period $T_A$. Alternatively, the measurement time period may be equal to or less than a time period $T_B$ in which the rate of change of the characteristic value remains within ±10% of the rate of change of the characteristic value at the time the accumulation of the analyte begins. The start of the measurement time period $T_B$ is preferably delayed for a short time period (which is less than the time period $T_B$) sufficient for the flow of fluid through the perforated structure to stabilize after a suction pump causing fluid containing the analyte is turned on and the analyte begins accumulating on the perforated structure.

When the characteristic value is compared with a threshold while a change in the characteristic value is small, the advantage of being able to predict a time when a large change in the characteristic value occurs and other advantages are obtainable. In the case where a high-concentration analyte is contained in the sample fluid, because the change in the characteristic value increases over time, a situation where the characteristic value exceeds the upper limit of quantification can be avoided by measuring the characteristic value at short time intervals.

A measurement system used in the present invention preferably includes a perforated structure having a pair of principal surfaces opposed to each other and having a plurality of cavity portions extending through both of the principal surfaces;

a pump causing a sample fluid containing the analyte to pass through the perforated structure whereby the analyte is accumulated on the perforated structure;

a detector for continuously detecting a characteristic value of the perforated structure as the analyte is accumulated thereon;

a timer measuring an elapsed time during which the analyte accumulates on the perforated structure; and a converter for converting the elapsed time for the characteristic value to reach a predetermined threshold into an amount of substance of the analyte.

First Embodiment

The amount of substance the analyte measured in the present embodiment is the concentration of a particulate matter (the analyte) suspended in a sample fluid whose diameters are typically close to 2.5 These particulates will be referred to hereinafter as PM2.5. The characteristic value of the perforated structure detected in the present embodiment is the rate of change of transmittance of electromagnetic waves through the perforated structure. The measurement method in the present embodiment is preferably implemented using the measurement system illustrated in FIG. 3.

An outline of the measurement method in the present embodiment is described with reference to the flow chart illustrated in FIG. 2. First, a pump is activated to cause the fluid holding the analyte to pass through the perforated structure and to begin accumulating the analyte on the perforated structure (S1). Then, the rate of change of transmittance of electromagnetic waves (which is one example of a characteristic value of the perforated structure) is continuously detected (S2) for at least a time period between the instant the pump is activated (S1) and the instant the pump is deactivated (S4). The rate of change of the transmittance of the electromagnetic waves are compared with a predetermined threshold each time the rate of change of transmittance (S3) is detected, and as long as the rate of change is less than the threshold, the detection of the rate of change (S2) is repeated.

When the rate of change becomes equal to or larger than the threshold (i.e., reaches the threshold), the pump is deactivated (S4), and the time elapsed from when the pump was activated (S1) (or a short time after it is activated which is sufficient to stabilize fluid flow though the perforated structure) until it is deactivated is measured (S5). Finally, the elapsed time is used to determine the amount of the analyte (S6) and measurement ends.

Figure 3:
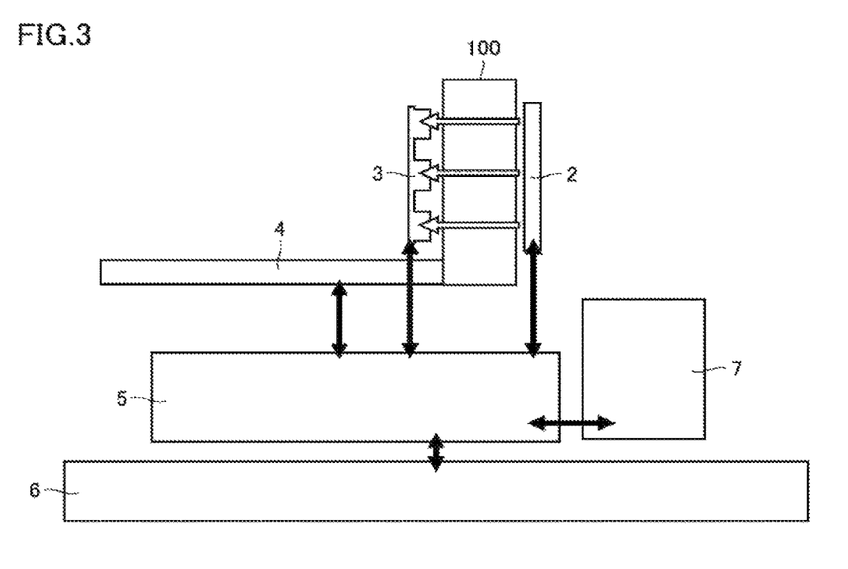
FIG. 3 is a schematic diagram for describing a measurement system used in the first embodiment.

Referring to FIG. 3, the measurement system used in the present embodiment preferably includes a cartridge 100, an electromagnetic wave source 2, an electromagnetic wave detector 3, a suction pump 4, a driving and controlling device 5, a battery 6, and a monitor 7. The driving and controlling device 5 is a device that can drive and control components, as indicated by the arrows connected therebetween illustrated in in FIG. 3.

In the measurement system of FIG. 3, a holding mechanism is made up of the cartridge 100, suction pump 4, driving and controlling device 5, and battery 6 and includes a mechanism for causing a sample fluid (atmosphere) containing an analyte to pass through the perforated structure. The amount of the analyte accumulated on the perforated structure increases with the passage of time (the pump operating time period).

A detection mechanism is made up of the cartridge 100, electromagnetic wave source 2, and electromagnetic wave detector 3 and can continuously detect the characteristic value of the perforated structure accumulating the analyte while the amount of the accumulated analyte increases.

The driving and controlling device 5 includes a time measuring mechanism (a timer which can be, for example, constructed as discrete hardware components or software run on a processor) for measuring the time elapsed from the time when accumulation of the analyte starts until the characteristic value reaches the predetermined value. The driving and controlling device 5 further includes a quantification mechanism (e.g., a computational unit which can be constructed, for example, as a programmed processor or an arithmetic unit) for determining the amount of substance of the analyte as a function of the elapsed time during which the analyte is accumulated.

The monitor 7 displays information required for measurement, such as a detected value of the rate of change of transmittance, the time elapsed, and the operating status of the pump. The battery 6 is electrically connected to all of the components other than the cartridge 100 to be able to supply them with electric power.

Figure 4:
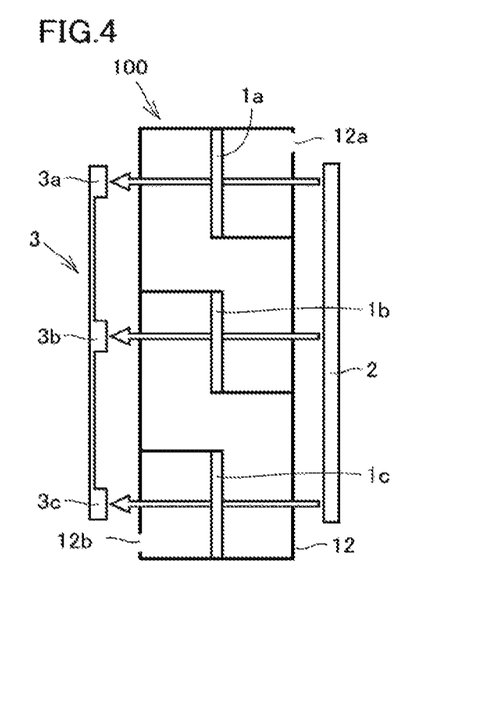
FIG. 4 is a partial enlarged view of FIG. 3.

FIG. 4 is a partial enlarged view that illustrates the cartridge 100 illustrated in FIG. 3 in an enlarged manner. The cartridge 100 includes a housing 12 having an air channel extending from an inlet 12a to an outlet 12b and three perforated structures 1a, 1b, and 1c arranged in the housing 12 such that they cross the path of the fluid flowing through the air channel and their principal surfaces adjacent to the inlet 12a are parallel to each other. The electromagnetic wave source 2 emits electromagnetic waves to the above-described arranged perforated structures 1a, 1b, and 1c. Electromagnetic waves that pass through the perforated structures are detected by electromagnetic wave detectors 3a, 3b, and 3c, and thus the characteristic values of the perforated structures can be detected. In the present embodiment, three perforated structures are used to accumulate and measure PM2.5. However, any number of the perforated structures can be used. The number of perforated structures used will be determined by the object to be measured or other factors. The first two perforated structures 1a, 1b are used to filter out relatively large particles and the third perforated structure 1c is used to accumulate the PM2.5 particles.

Figure 5A:
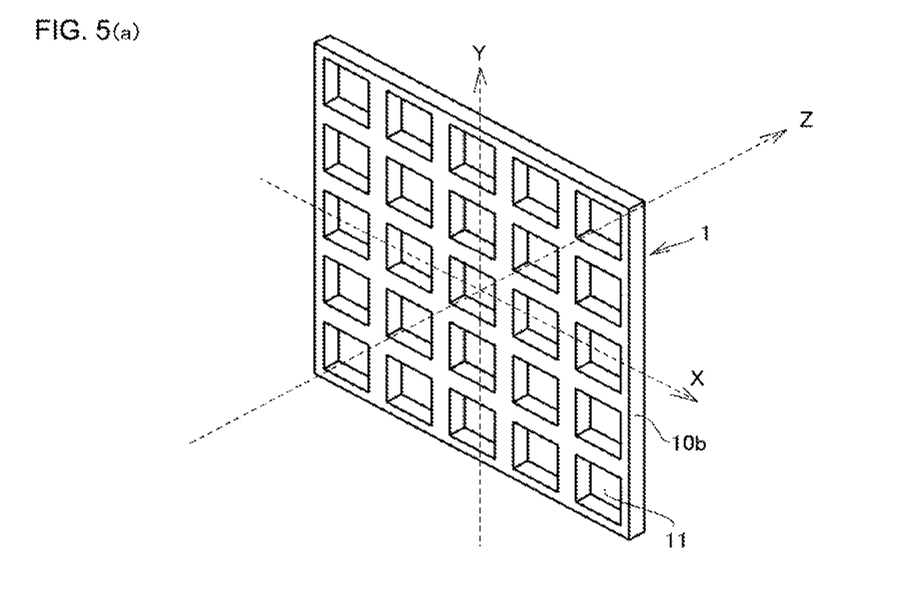
FIGS. 5(a) and 5(b) are schematic diagrams for describing an example of a perforated structure used in the first embodiment.
Figure 5B:
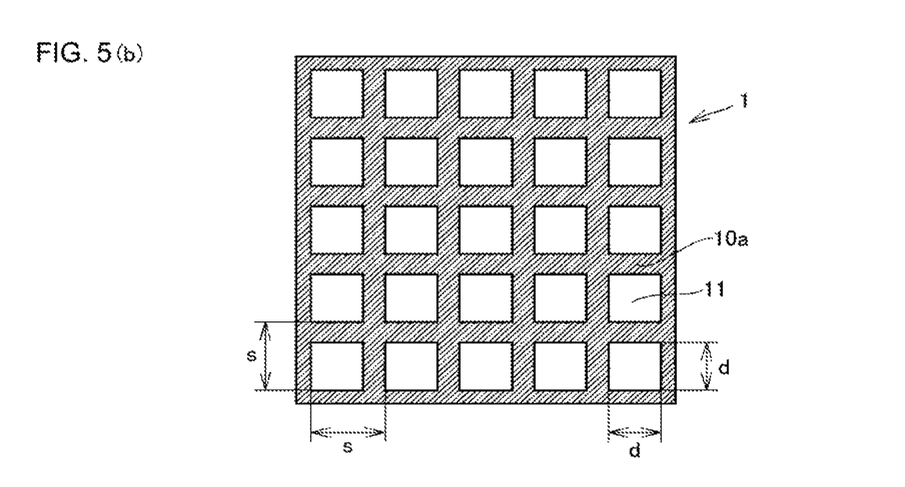

The perforated structures 1a, 1b, and 1c are typically round mesh structures having a diameter of 6 mm. As shown in FIGS. 5(a) and 5(b) (which show square subsections of the preferably round perforated structures), the perforated structures preferably have square cavity portions arranged in a tetragonal lattice array in a mesh portion (perforated portion) where the cavity portions are arranged. For the perforated structure 1a, the lattice interval ("s" illustrated in FIG. 5(b)) is preferably 260 µm, the hole size ("d" illustrated in FIG. 5(b)) is preferably 180 µm, and the film thickness (the thickness of the perforated structure as measured in the horizontal direction of FIG. 4) is preferably 20 µm. For the perforated structure 1b, the lattice interval is preferably 6.0 µm, the hole size is preferably 4.2 µm, and the film thickness is preferably 2 µm. For the perforated structure 1c, the lattice interval is preferably 2.6 µm, the hole size is preferably 1.8 µm, and the film thickness is preferably 1.2 µm.

In that way, three types of perforated structures having different hole sizes, etc. are arranged in series inside the housing 12. Thus, when the suction pump 4 is driven and the fluid flows inside the cartridge 100 from the inlet 12a to outlet 12b, particulate matter larger than PM2.5 pass are filtered out by the perforated structures 1a and 1b and only PM2.5 is accumulated in any significant amounts on the perforated structure 1c. The matter larger than PM2.5 which is accumulated on the perforated structures 1a and 1b can also be measured. When various hole sizes in perforated structures and structural designs are combined, the present embodiment can also be applied to uses other than detection of PM2.5.

The perforated structure used in the present embodiment preferably includes a pair of opposed principal surfaces and has a plurality of cavity portions extending through the opposed principal surfaces. The plurality of cavity portions are preferably arranged periodically in the principal surfaces of the perforated structure in at least one direction. All the cavity portions may be arranged periodically. Alternatively, some of the cavity portions may be arranged periodically, whereas the other cavity portions may be arranged non-periodically within a range where the advantages of the present invention are not lost.

The perforated structure may preferably be a quasi-periodic structure or periodic structure. The quasi-periodic structure is a structure that does not have translational symmetry but maintains order in the array. Examples of the quasi-periodic structure may include a Fibonacci structure as a one-dimensional quasi-periodic structure and a Penrose structure as a two-dimensional quasi-periodic structure. The periodic structure is a structure having spatial symmetry, typified by translational symmetry, and can be classified into one-dimensional periodic structure, two-dimensional periodic structure, and three-dimensional periodic structure, depending on the dimension of symmetry. Examples of the one-dimensional periodic structure may include a wire-grid structure and one-dimensional diffraction grating. Examples of the two-dimensional periodic structure may include a mesh filter and two-dimensional diffraction grating. Among those periodic structures, the two-dimensional periodic structure may suitably be used.

One example of the two-dimensional periodic structure may be a planar structure (lattice structure) in which cavity portions are arranged at constant intervals in a matrix as illustrated in FIG. 5. The perforated structure 1 illustrated in FIG. 5(a) is a planar structure in which square cavity portions 11 are spaced uniformly in two array directions parallel to the sides of the squares (vertical and horizontal directions in the drawing), as seen in a direction perpendicular to a principal surface 10a thereof. The general shape of the perforated structure may typically be a plate-like shape or film-like shape. The cavity portions are not limited to the above-described shape. Examples of the shape of the cavity portion may include a rectangle, circle, and ellipse. The shape is also not limited to the above-described symmetrical shapes. When the cavity portions are arranged in a quadrilateral array, the intervals in the two array directions may be different, and a rectangular array may be used.

The thickness (t) of the perforated structure is preferably between $\frac{1}{10}$ of wavelength $\lambda$ of electromagnetic waves used in measurement and 10 times the wavelength $\lambda$, and more preferably, between 0.3 µm and 30 µm. In measurement using electromagnetic waves, if the thickness of the perforated structure exceeds that range, it may be difficult to detect signals because the strength of electromagnetic waves having passed therethrough or been reflected thereat is weak.

For example, preferably, the size (d) of an aperture portion in the perforated structure may be between $\frac{1}{10}$ of the wavelength $\lambda$ of the electromagnetic waves used in measurement and 10 times the wavelength $\lambda$, and more preferably, between 0.3 µm and 30 µm. In measurement using electromagnetic waves, if the size (d) of the aperture portion of the perforated structure exceeds that range, it may be difficult to detect signals because the strength of electromagnetic waves having passed therethrough or been reflected thereat is weak.

The perforated structure may preferably be made of metal. When precious metal (preferably gold) is used as the metal, because the conductivity of the perforated structure increases and large transmittance is obtainable (in particular, in the case where the aperture size in the perforated structure is small), analysis in detection using electromagnetic waves is facilitated. From the viewpoint of cost, the metal may preferably contain non-precious metal. For example, it may preferably be made of non-precious metal or made of an alloy of non-precious metal and another metal. It may preferably be metal that allows a hydroxy group to be formed on its surface. Examples of such non-precious metal may include nickel, stainless steel, titanium, tungsten, iron, chrome, silicon, and germanium, and preferably, it may be nickel, stainless steel, or titanium.

As noted above, the characteristic value of the perforated structure holding the analyte is continuously detected during at least a part of the time period beginning when the pump is turned on and ending when the pump is turned off.

The expression "the characteristic value is continuously detected" means that the characteristic value is detected regularly and includes intermittent detection. The detection may start when the analyte begins accumulating on the perforated structure, after the analyte begins accumulating on the perforated structure, or before the analyte beings accumulating on the perforated structures. The detection may end when accumulation of the analyte stops (e.g., when the suction pump is turned off), after accumulation of the analyte stops or before accumulation of the analyte stops. From the viewpoint of measurement efficiency, the detection may preferably end at an early stage of the period during which the analyte is accumulated.

Figure 2:
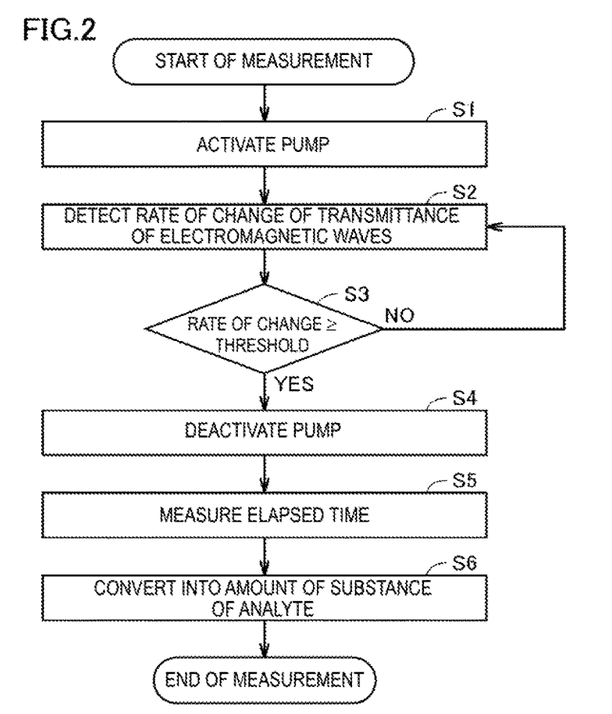
FIG. 2 is a flow chart that illustrates a procedure in a measurement method according to a first embodiment.

As described above with reference to the flow chart illustrated in FIG. 2, the characteristic value is compared with the predetermined threshold (S3) for each detection of the characteristic value. When the characteristic value is less than the threshold, the detection of the characteristic value repeats (S2). When the characteristic value becomes equal to or larger than the threshold (reaches the threshold), accumulation of the analyte ends (S4), and the time elapsed from the start of accumulating the analyte (S1) is measured (S5).

In the measurement method in the present embodiment, although continuous detection increases the number of detections, the frequency characteristics can be detected while the perforated structure accumulating the analyte is in an unchanged state without being moved or the like. Thus, the problem of decreasing the working efficiency does not easily arise.

To determine the amount of the analyte accumulated, the time elapsed from the time when flow of the fluid begins (and accumulation of the analyte starts) to the time when the rate of change of transmittance (characteristic value) of the perforated structure reaches the threshold is converted into (i.e., used to determine) the amount of substance of the analyte.

One example method for converting the elapsed time into the amount of substance of the analyte is described below. First, predetermined characteristic values for the perforated structures holding various quantities of the analyte are continuously detected in advance. Then, a plurality of primary calibration curves indicating the relationships between the characteristic values and elapsed times for each amount of substance of the analyte are created on the basis of data on the obtained characteristic values, and from the primary calibration curves, a secondary calibration curve indicating a relationship between the amount of substance of the analyte and the elapsed time to the time when the characteristic value of the perforated structure reaches the predetermined threshold is created. By using that secondary calibration curve, the elapsed time can be converted into (used to determine) the amount of substance of the analyte.

Figure 6:
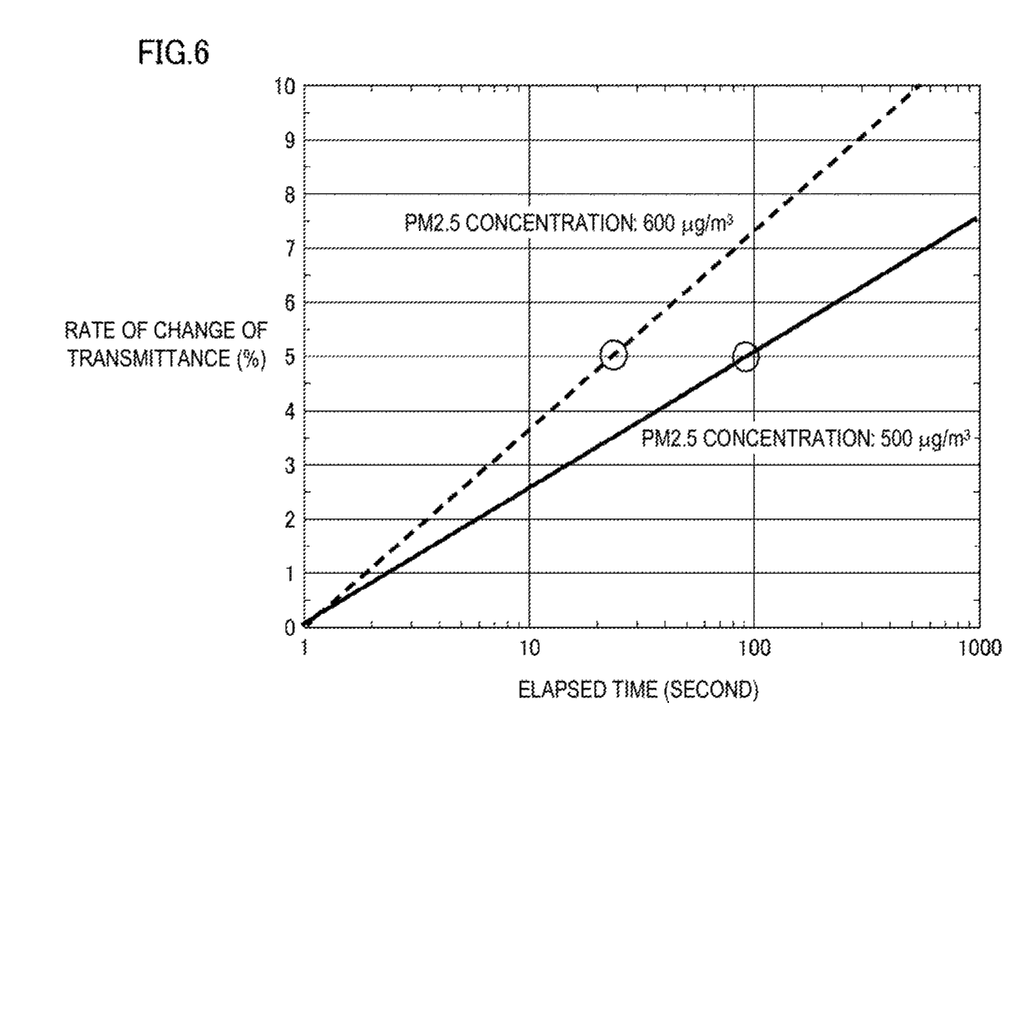
FIG. 6 illustrates an example of primary calibration curves in the first embodiment.
Figure 7:
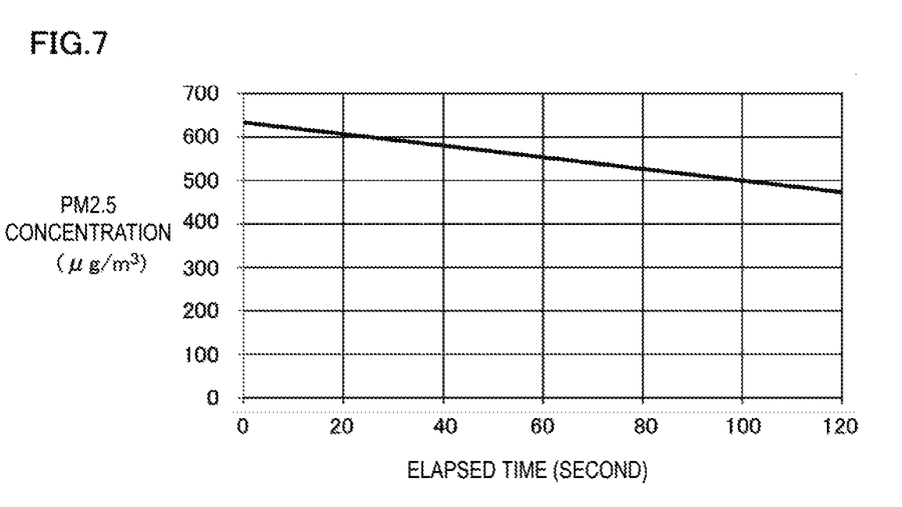
FIG. 7 illustrates an example of a secondary calibration curve in the first embodiment.

For example, a standard fluid in which the air contains a concentration of 500 μg/m3 of PM2.5 and a standard fluid in which the air contains a concentration of 600 μg/m3 of PM2.5 are prepared, each of the standard fluids is caused to pass through the perforated structures 1a, 1b, and 1c illustrated in FIG. 4 at a predetermined flow velocity, and the rate of change of transmittance of electromagnetic waves is detected continuously (e.g., at intervals of 0.1 seconds) is detected in advance. A primary calibration curve indicating the relationship between the rate of change of transmittance of electromagnetic waves and the elapsed time is created for each concentration of PM2.5 on the basis of data on the obtained rates of change in transmittance of electromagnetic waves (see FIG. 6). From the primary calibration curves illustrated in FIG. 6, the time elapsed to the time when the rate of change of transmittance of electromagnetic waves of the perforated structure reaches the predetermined threshold (e.g., 5%) for each concentration of PM2.5 is determined, and on the basis of the results, a secondary calibration curve indicating a relationship between the concentration of PM2.5 and the elapsed time can be created (see FIG. 7). That is, FIG. 7 illustrates the relationship between the concentration of PM2.5 and the time elapsed to the time when the rate of change of transmittance reaches 5%. By using the secondary calibration curve obtained in the above-described way, the elapsed time can be converted into the amount of substance of the analyte. Here, for the sake of simplification of description, two kinds of concentrations of PM2.5 are prepared. If additional standard fluids with different concentrations of PM2.5 are prepared and preliminary measurement is conducted, the accuracy of the secondary calibration curve can be improved, and the accuracy of the measurement can be increased.

As described above, when the transmittance of electromagnetic waves reaches the predetermined threshold before the predetermined time at which measurement of the characteristic value is to end, the time elapsed to the time when the transmittance of electromagnetic waves reaches the threshold is converted into the amount of substance of the analyte. In the case where the transmittance of electromagnetic waves does not reach the predetermined threshold before the predetermined time period elapses, one example may be that the amount of substance of the analyte is determined to be less than a predetermined lower limit of quantification.

Measurement Example 1

One example measurement by the measurement method in the first embodiment is described below. The characteristic value of the perforated structure to be detected was defined as the rate of change of transmittance of electromagnetic waves when predetermined electromagnetic waves are emitted to the perforated structure (rate of change to the transmittance in only the perforated structure 1c on which PM2.5 has accumulated), and the threshold was set as 5%. After activation of the suction pump 4, the rate of change of transmittance of electromagnetic waves in the perforated structure 1c was continuously detected (e.g., at intervals of 0.1 seconds). At the time when the rate of change reached 5%, the suction pump was shut off, and the detection ended.

The time elapsed from the activation of the suction pump 4 at the time when the rate of change reaches 5% was 100 seconds. The secondary calibration curve obtained from the preliminary measurement revealed that in the case where the concentration of PM2.5 contained in the atmosphere was 500 μg/m3, when suction was performed for 100 seconds, the rate of change of transmittance of electromagnetic waves was 5%. Accordingly, the elapsed time of 100 seconds was converted into the concentration of 500 μg/m3 of PM2.5. Therefore, the concentration of PM2.5 contained in the atmosphere was quantified into 500 μg/m3.

A similar measurement was performed on another day. The result was that the elapsed time at the time when the rate of change of transmittance of electromagnetic waves reached 5% was 22 seconds. The secondary calibration curve obtained from the preliminary measurement revealed that in the case where the concentration of PM2.5 contained in the atmosphere was 600 μg/m3, when suction was performed for 22 seconds, the rate of change of transmittance of electromagnetic waves was 5%. Accordingly, the concentration of PM2.5 contained in the atmosphere was determined to be 600 μg/m3.

Comparative Measurement Example 1

The concentration of PM2.5 in the atmosphere (fluid) was measured in the same manner as in the above-described Measurement Example 1, except that the threshold for the transmittance of electromagnetic waves was not set, the suction pump was operated for 100 seconds, and the rate of change of transmittance of electromagnetic waves after 100 seconds was measured.

In the case where the concentration of PM2.5 was 500 μg/m3, 5% was detected as the rate of change of transmittance, and the concentration of PM2.5 was quantified (determined). In contrast, in the case where the concentration of PM2.5 was 600 μg/m3, the transmittance was 0% (the state in which signals for the transmittance were unobtainable). That is, the concentration of PM2.5 exceeded the upper limit of quantification, and the concentration of PM2.5 was not correctly quantified. When the perforated structure was observed visually in the case where the concentration of PM2.5 was 600 μg/m3, the surface was fully white, and a large quantity of PM2.5 was accumulated. In that case, although measurement can be performed again with a shortened operating time of the suction pump, because the measurements are performed twice, the entire measurement is inefficient.

In contrast, according to the measurement method in the first embodiment, even in the case where a traditional method, as in the comparative measurement example, cannot support changes in the amount of substance of the analyte, measurement can be performed with high precision by one measurement method without causing inefficiency, such as extension of a time required for the entire measurement.

Second Embodiment

The present embodiment differs from the first embodiment in that during the accumulating step, the amount of suction of the suction pump is feedback controlled on the basis of a result of detection of the characteristic value of the perforated structure and thus the flow velocity of a sample fluid (atmosphere) is optimized by increasing or decreasing the flow of velocity as appropriate. In the other respects, the present embodiment is basically the same as the first embodiment.

Figure 8:
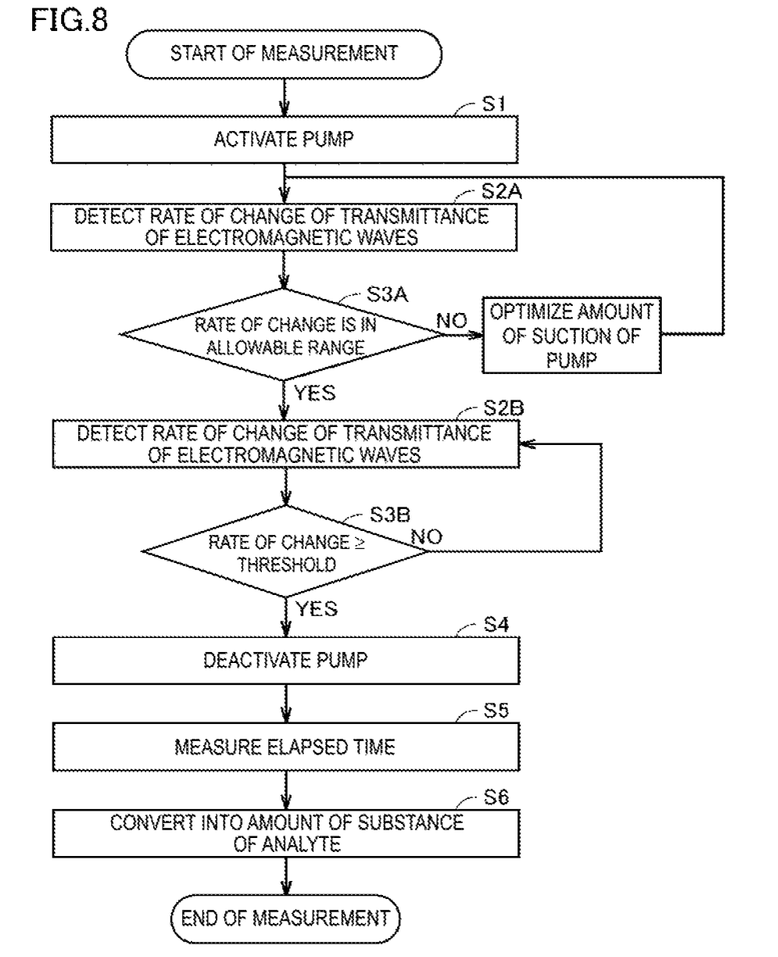
FIG. 8 is a flow chart that illustrates a procedure in a measurement method according to a second embodiment.

An outline of a measurement method in the present embodiment is described with reference to the flow chart in FIG. 8. First, as in the case of the first embodiment, the pump is activated (S1) to cause the atmosphere to pass through the perforated structure and to thereby start accumulation of the analyte.

Next, the rate of change of transmittance of electromagnetic waves in the perforated structure is detected (S2A). This can begin as soon as the pump is turned on or after a predetermined management time period during which flow through housing 12 is stabilized. When the rate of change of the characteristic value is not within a predetermined allowable range, the suction created by suction of the pump is optimized (increased or decreased). For example, in the case where the rate of change of the characteristic value is less than the allowable range, the amount of suction created by the pump will be increased and the time elapsed from the moment the pump is turned on to the time when the characteristic value reaches the threshold will be shortened. This increases the efficiency in which measurement of the concentration of the analyte can be performed. When the rate of change of the characteristic value exceeds the allowable range, the amount of suction created by the pump will be reduced and it will be possible to prevent an increase in error factors caused by significantly shortening the time elapsed to the time when the characteristic value reaches the threshold. As a result, a higher precision of measurement of the concentration of the analyte can be achieved. When the rate of change of the characteristic value is in the predetermined allowable range, the rate of change of transmittance is continuously detected (S2B) without changing the amount of suction created by the suction pump.

Next, as in the case of the first embodiment, the characteristic value is compared with the predetermined threshold each time the rate of change is detected (S3B). If the characteristic value is less than the threshold, the detection of the characteristic value is repeated (S2). If the characteristic value becomes equal to or greater than the threshold (reaches the threshold), the pump is deactivated (S4).

In the present embodiment elapsed time (S5) must be measured differently depending on whether or not the suction level of the pump was changed. When the rate of change was in the allowable range at S3A and the amount of suction of the pump was not changed, as in the case of the first embodiment, the time elapsed from the activation of the pump (S1) (or after the short flow stabilizing delay) to the time the pump is turned off (S4) is measured. When the rate of change of the characteristic value was outside the allowable range at S3A and the amount of suction of the pump was increased or decreased, the two time periods (the time period before the amount of suction of the pump was changed and after it) must be normalized. To that end, the total time period from the moment the pump is turned on (or after the short flow stabilizing delay) to the moment it is turned off is calculated as (1) the time period from when the pump is turned on (or after the short flow stabilizing delay) and ending when the suction of the pump was changed and (2) the time period beginning when the suction of the pump was changed and ending when the pump is turned off times the ratio between the suction force before the suction of the pump was changed to the suction force after the suction of the pump was changed.

After the (adjusted) total time has been calculated, the concentration of the analyte is determined as a function of the elapsed time (i.e., the total elapsed time is converted to the concentration of the analyte) at (S6). This ends the measurement process.

In the present embodiment, the time required for the entire measurement can be shortened, and measurement with higher efficiency can be performed.

Third Embodiment

The present embodiment differs from the first embodiment in that the characteristic value of the perforated structure to be detected is the flow velocity, quantity of flow, or pressure loss of the sample fluid (atmosphere). In the other respects, the present embodiment is basically the same as the first embodiment.

An outline of a measurement method in the present embodiment is described with reference to the flow chart in FIG. 9. First, the pump is activated to start accumulating the analyte, and the sample fluid (atmosphere) is caused to pass through the perforated structure (S1). Then, the rate of change of flow velocity of the sample fluid is continuously detected (S2) for at least a fixed time period in a period from the time when the pump is activated to the time when the pump is deactivated (S4). The rate of change of flow velocity of the sample fluid is one example of the characteristic value of the perforated structure. The sucking force of the pump is maintained constant. The rate of change of the flow velocity is compared with the predetermined threshold each time the rate of change of flow velocity is detected (S3). When the rate of change is less than the threshold, the process returns to step S2 and the rate of change is again detected.

When the rate of change becomes equal to or larger than the threshold (reaches the threshold), the pump is deactivated (S4), and the time elapsed from the activation of the pump (S1) is measured (S5). Finally, the elapsed time is converted into the amount of substance of the analyte (S6), and the measurement ends.

Figure 10:
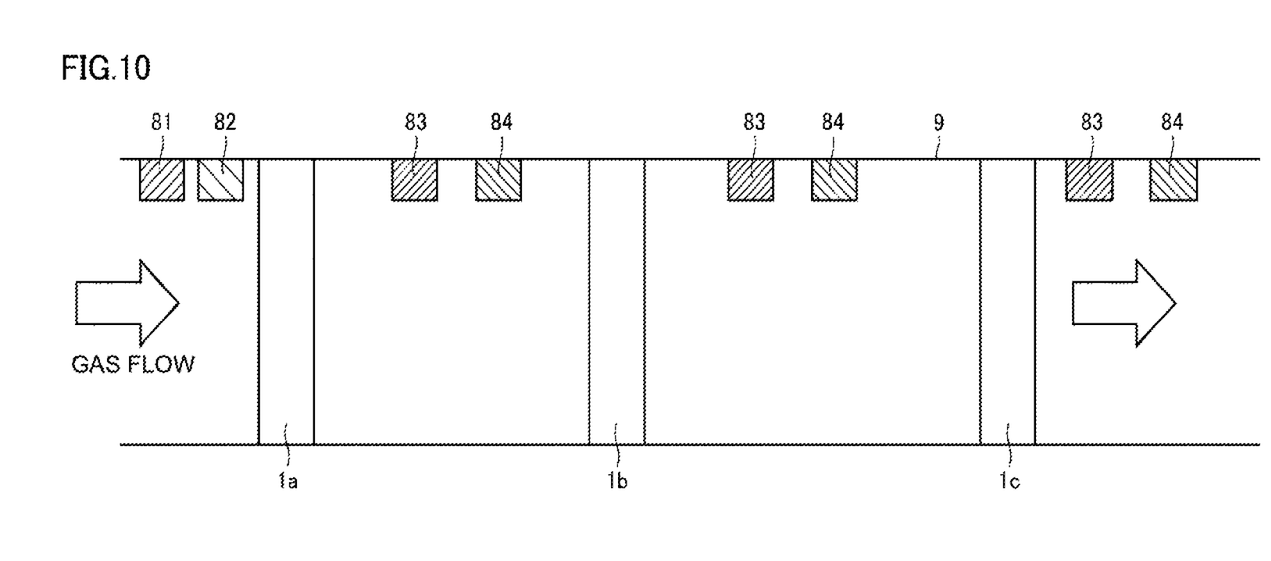
FIG. 10 is a schematic diagram for describing a measurement system used in the third embodiment.

An example measurement system used in the present embodiment is a system in which the cartridge 100, the electromagnetic wave source 2, and the electromagnetic wave detector 3 in the measurement system in the first embodiment are replaced with a cylindrical member 9 illustrated in FIG. 10. Referring to FIG. 10, the inside of the cylindrical member 9 is a channel through which the atmosphere may flow. The perforated structures 1a, 1b, and 1c are arranged in series from the upstream side in that channel. A temperature sensor 81, a humidity sensor 82, flow velocity sensors 83, and pressure sensors 84 are disposed on an inner wall of the cylindrical member 9 as shown.

Figure 9:
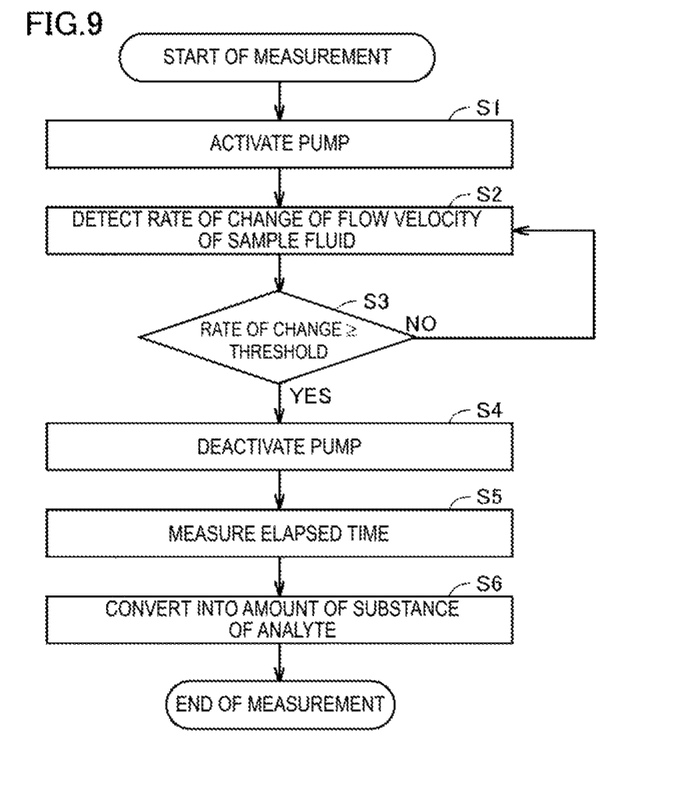
FIG. 9 is a flow chart that illustrates a procedure in a measurement method according to a third embodiment.

In the above description using the flow chart illustrated in FIG. 9, the case where the characteristic value of the perforated structure is the rate of change of flow velocity of the sample fluid measured by the flow velocity sensor 83 is described. The characteristic value of the perforated structure detected in the present embodiment may be the rate of change of temperature measured by the temperature sensor 81, the rate of change of humidity measured by the humidity sensor 82, or the rate of change of pressure measured by the pressure sensor 84.

In the case where the characteristic value being an object to be detected is the flow velocity or pressure, the loss (loss in the quantity of flow, pressure loss) resulting from accumulating (trapping) the analyte in the perforated structure can be determined, feedback can be provided to the suction pump, the flow velocity or pressure can be made constant, and thus, the measurement can be utilized for maintaining performance of the measurement system. In addition, with the aim of maintaining the flow velocity, quantity of flow, or pressure, the rate of change of electric power (current or voltage) input into the pump can also be used as one example of the characteristic value.

The embodiments disclosed this time must be considered as illustrative in all points and not restrictive. The range of the present invention is shown not by the above description but by the scope of claims for patent, and it is intended that all modifications within the meaning and range equivalent to the scope of claims for patent are included.

REFERENCE SIGNS LIST

1, 1a, 1b, 1c perforated structure, 10a principal surface, 11 cavity portion, 12 housing, 12a inlet, 12b outlet, 100 cartridge, 2 electromagnetic wave source, 3 electromagnetic wave detector, 4 suction pump, 5 driving and controlling device, 6 battery, 7 monitor, 81 temperature sensor, 82 humidity sensor, 83 flow velocity sensor, 84 pressure sensor, 9 cylindrical member.

The invention claimed is:

1. A method for measuring the concentration of an analyte in a fluid, comprising:
   accumulating the analyte on a perforated structure by causing fluid to pass through the perforated structure, the perforated structure having a pair of principal surfaces opposed to each other and having a plurality of cavity portions extending through both of the principal surfaces;
   measuring a time period during which the analyte is accumulated on the perforated structure, the time period ending when a characteristic value of the perforated structure reaches a predetermined threshold; and
   determining the concentration of the analyte in the sample fluid as a function of the measured time period.

2. The method of claim 1, wherein the velocity of the fluid passing through the perforated structure is optimized as a function of the measured characteristic value of the perforated structure.

3. The method of claim 2, wherein the velocity of the fluid passing through the perforated structure is optimized as a function of the rate of change of the characteristic value of the perforated structure.

4. The method of claim 3, wherein the velocity of the fluid passing through the perforated structure is increased when the rate of change of the characteristic value of the perforated structure is below a first predetermined value and is decreased when the rate of change of the characteristic value of the perforated structure is above a second predetermined value.

5. The method of claim 4, wherein the concentration of the analyte in the sample fluid is determined as a function of both the measured time period and the portions of the measured time period before and after the optimization of the velocity of the fluid passing through the perforated structure takes place.

6. The method of claim 1, wherein the characteristic value is a parameter relating to frequency characteristics of electromagnetic waves passing through the perforated structure.

7. The method of claim 1, wherein the characteristic value comprises one or more of a velocity of the fluid passing through the perforated structure, a quantity of flow of fluid passing through the perforated structure, and a pressure loss occurring when the fluid passes through the perforated structure.

8. The method of claim 1, wherein the concentration of the analyte in the sample fluid is determined as a function of the measured time period by comparing the measured time period to a transfer curve which is based upon premeasurements of known fluid concentrations.

9. Apparatus for measuring the concentration of an analyte in a fluid, comprising:
   a perforated structure having a pair of principal surfaces opposed to each other and having a plurality of cavity portions extending through both of the principal surfaces;
   means for passing the fluid through the perforated structure such that the analyte accumulates on the perforated structure;
   means for measuring a time period during which the analyte is accumulated on the perforated structure, the time period ending when a characteristic value of the perforated structure reaches a predetermined threshold; and
   means for determining the concentration of the analyte in the sample fluid as a function of the measured time period.

10. The apparatus of claim 9, wherein the means for passing the fluid through a perforated structure causes the velocity of the fluid passing through the perforated structure to be optimized as a function of the measured characteristic value of the perforated structure.

11. The apparatus of claim 10, wherein the means for passing the fluid through a perforated structure causes the velocity of the fluid passing through the perforated structure to be optimized as a function of the rate of change of the characteristic value of the perforated structure.

12. The apparatus of claim 11, wherein the means for passing the fluid through a perforated structure causes the velocity of the fluid passing through the perforated structure to be increased when the rate of change of the characteristic value of the perforated structure is below a first predetermined value and to be decreased when the rate of change of the characteristic value of the perforated structure is above a second predetermined value.

13. The apparatus of claim 11, wherein the means for determining the concentration of the analyte in the sample fluid determines the concentration of the analyte as a function of both the measured time period and the portions of the measured time period before and after the optimization of the velocity of the fluid passing through the perforated structure takes place.

14. The apparatus of claim 9, wherein the characteristic value is a parameter relating to frequency characteristics of electromagnetic waves passing through the perforated structure.

15. The apparatus of claim 9, wherein the characteristic value comprises one or more of a velocity of the fluid passing through the perforated structure, a quantity of flow of fluid passing through the perforated structure, and a pressure loss occurring when the fluid passes through the perforated structure.

16. The apparatus of claim 9, wherein the means for determining the concentration of the analyte in the sample fluid determines the concentration of the analyte as a function of the measured time period by comparing the measured time period to a transfer curve which is based upon premeasurements of known fluid concentrations.

\* \* \* \* \*